United States Patent
Ichitani et al.

(10) Patent No.: US 9,558,393 B2
(45) Date of Patent: Jan. 31, 2017

(54) IMAGE PROCESSING DEVICE AND STORAGE MEDIUM FOR IMAGE PROCESSING

(71) Applicant: Konica Minolta, Inc., Tokyo (JP)

(72) Inventors: Shuji Ichitani, Hachioji (JP); Osamu Toyama, Kakogawa (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/778,427

(22) PCT Filed: Mar. 27, 2014

(86) PCT No.: PCT/JP2014/058725
§ 371 (c)(1),
(2) Date: Sep. 18, 2015

(87) PCT Pub. No.: WO2015/145644
PCT Pub. Date: Oct. 1, 2015

(65) Prior Publication Data
US 2016/0275673 A1    Sep. 22, 2016

(51) Int. Cl.
*G06K 9/00* (2006.01)
*G06T 7/00* (2006.01)
(Continued)

(52) U.S. Cl.
CPC ............ *G06K 9/00127* (2013.01); *G01N 1/30* (2013.01); *G06K 9/0014* (2013.01);
(Continued)

(58) Field of Classification Search
CPC .................. G06T 7/0012; G06T 2207/10064; G06T 2207/10056; G06T 2207/10061; G06T 2207/20141; G06T 2207/20212; G06T 2207/20221; G06T 2207/30024; G06K 9/00127; G06K 9/00134; G06K 9/0014; G06K 9/4604; G01N 1/30

See application file for complete search history.

(56) References Cited

U.S. PATENT DOCUMENTS 6,215,892 B1 *   4/2001   Douglass ............... G01N 1/312
                                                       382/128
7,113,625 B2 *   9/2006   Watson .................. G06F 19/321
                                                       382/128
(Continued)

FOREIGN PATENT DOCUMENTS

JP    2001269195 A    10/2001
JP    2005524090 A    8/2005
(Continued)

OTHER PUBLICATIONS

International Search Report dated Jun. 24, 2014 for PCT/JP2014/058725 (no English translation available).
(Continued)

*Primary Examiner* — Manav Seth
(74) *Attorney, Agent, or Firm* — Lucas & Mercanti, LLP

(57) ABSTRACT

An image processing device inputs a bright field linage of a tissue slice in which a cell nucleus is stained and a fluorescent image of the tissue slice in which a specific biological substance is stained with a fluorescent staining reagent (S10), extracts a cell nucleus from the image of the cell nucleus (S20), extracts a fluorescent bright point from the fluorescent image (S30), specifies a cell nucleus to which the fluorescent bright point is assigned on the basis of the distance between the cell nucleus and the fluorescent bright point, and assigns the fluorescent bright point with the cell nucleus (S40).

9 Claims, 15 Drawing Sheets

(51) Int. Cl.
*G06K 9/46* (2006.01)
*G01N 1/30* (2006.01)
(52) U.S. Cl.
CPC ....... *G06K 9/00134* (2013.01); *G06K 9/4604* (2013.01); *G06T 7/0012* (2013.01); *G06T 2207/10056* (2013.01); *G06T 2207/10061* (2013.01); *G06T 2207/10064* (2013.01); *G06T 2207/20212* (2013.01); *G06T 2207/30024* (2013.01)

(56) References Cited

U.S. PATENT DOCUMENTS

| | | | | |
|---|---|---|---|---|
| 7,697,755 | B2* | 4/2010 | Lee | G06K 9/00127 382/133 |
| 7,933,435 | B2* | 4/2011 | Hunter | G06K 9/00127 382/128 |
| 8,199,999 | B2* | 6/2012 | Hoyt | G01N 1/30 382/133 |
| 8,335,374 | B2* | 12/2012 | Boardman | G06T 7/0012 382/165 |
| 8,379,962 | B2* | 2/2013 | Hoyt | G01N 1/30 382/133 |
| 8,428,331 | B2* | 4/2013 | DiMarzio | G02B 21/0004 382/133 |
| 8,744,164 | B2* | 6/2014 | Ozinsky | G01N 21/6458 348/79 |
| 9,176,043 | B2* | 11/2015 | Takagi | G01N 15/1475 |
| 9,189,678 | B2* | 11/2015 | Tsunomori | G06T 7/0012 |
| 9,355,445 | B2* | 5/2016 | Yamashita | A61B 5/055 |
| 9,384,550 | B2* | 7/2016 | Mimura | G06T 7/60 |
| 9,435,738 | B2* | 9/2016 | Wirtz | G01N 21/6458 |
| 2002/0081014 | A1* | 6/2002 | Ravkin | G01N 15/1475 382/134 |
| 2003/0231791 | A1* | 12/2003 | Torre-Bueno | G01N 21/6428 382/133 |
| 2005/0163359 | A1* | 7/2005 | Murao | G01N 15/1475 382/128 |
| 2005/0265588 | A1* | 12/2005 | Gholap | G06K 9/00127 382/128 |
| 2010/0172569 | A1* | 7/2010 | Takagi | G01N 15/1475 382/133 |
| 2011/0170754 | A1* | 7/2011 | Yoshihara | G06T 7/0012 382/128 |
| 2011/0249883 | A1* | 10/2011 | Can | G06K 9/0014 382/133 |
| 2011/0254943 | A1* | 10/2011 | Ozinsky | G01N 21/6458 348/79 |
| 2013/0094733 | A1* | 4/2013 | Nosato | G06K 9/4671 382/128 |
| 2015/0049936 | A1* | 2/2015 | Tsunomori | G01N 21/6456 382/133 |
| 2016/0163043 | A1* | 6/2016 | Mimura | G06T 7/60 382/133 |

FOREIGN PATENT DOCUMENTS

| | | |
|---|---|---|
| JP | 2007147563 A | 6/2007 |
| JP | 2009115599 A | 5/2009 |
| JP | 2012198139 A | 10/2012 |
| JP | 2013057631 A | 3/2013 |
| WO | 2013146843 A1 | 10/2013 |

OTHER PUBLICATIONS

IPRP dated Sep. 27, 2016 from the PCT Application; International application No. PCT/JP2014/058725; English translation of IPRP; Total of 11 pages.

* cited by examiner

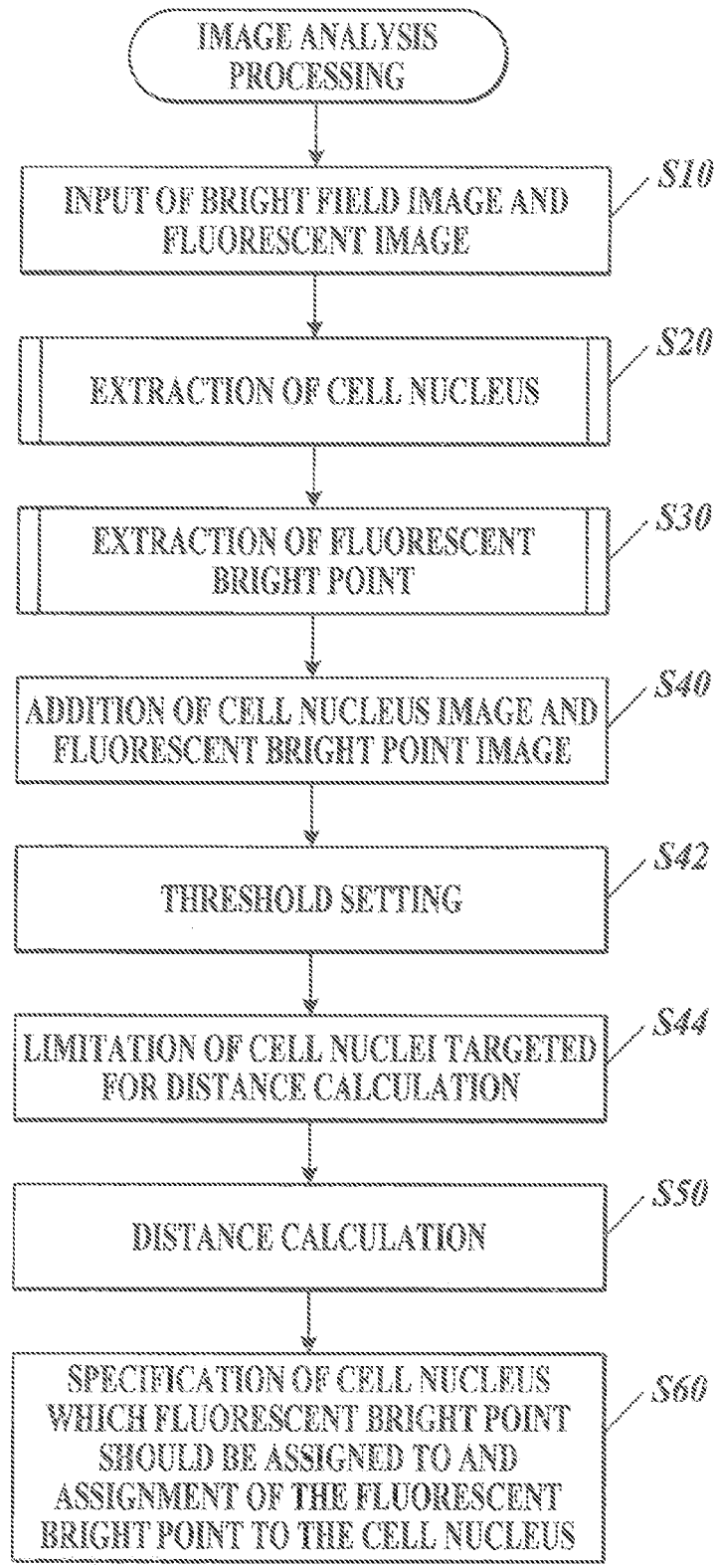

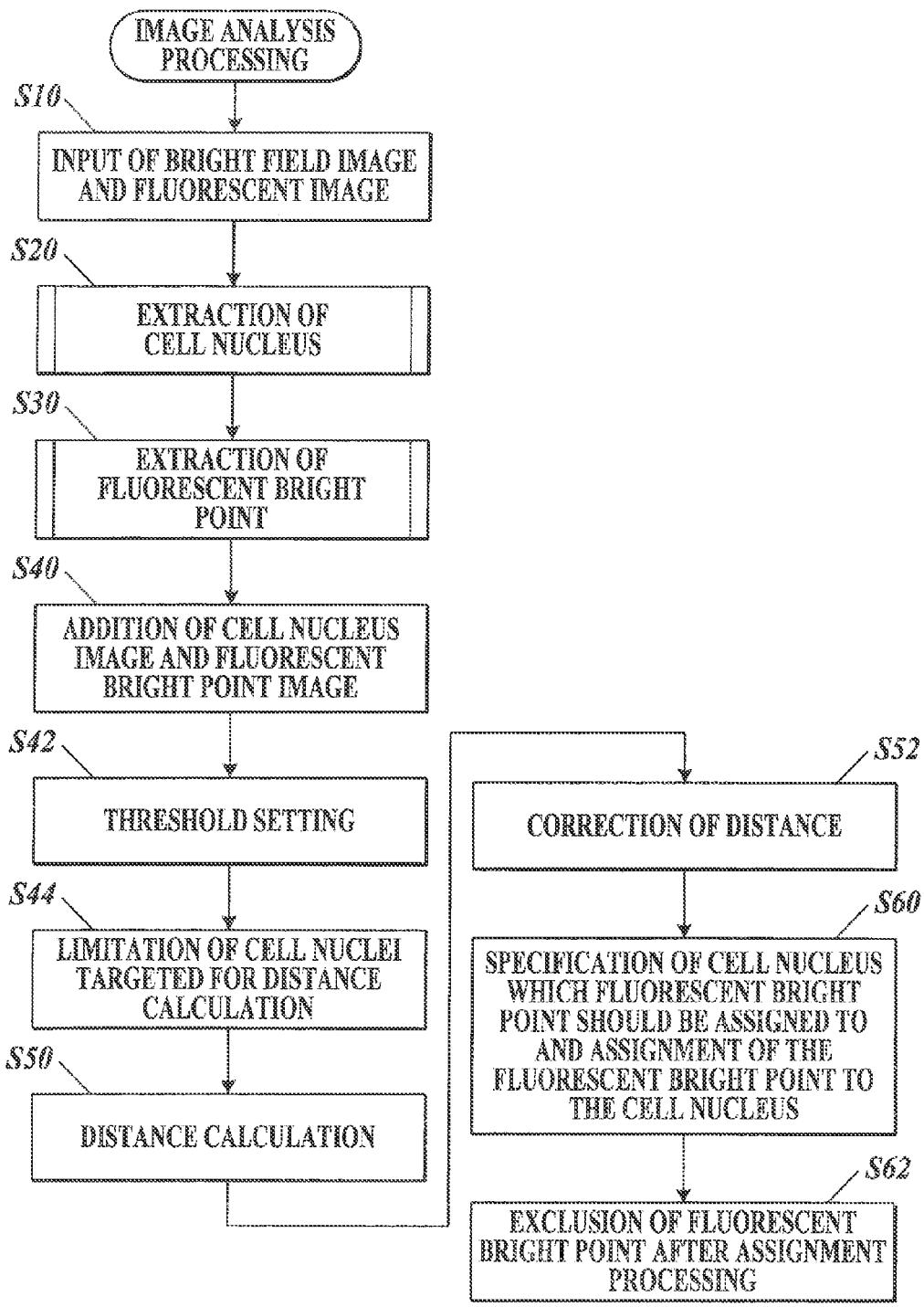

ically, according to the technique described in Patent Document 2, a bright field image of a tissue slice processed for HE staining is acquired, a cell nucleus region is extracted from the bright field image, a region of a prescribed distance from a centroid of the extracted cell nucleus region is estimated as a cell region, and the expression level of a biological substance in the cell region is determined on the basis of the cell nucleus and the number of fluorescent bright points includes within the cell region (see paragraphs 0092 to 0104, FIG. 20A, paragraph 0128, etc.).

PRIOR ART LITERATURES

Patent Literature

Patent Document 1: Japanese Patent Application Publication No. 2013-057631
Patent Document 2: International Patent Application Publication No. 2013/146843

IMAGE PROCESSING DEVICE AND STORAGE MEDIUM FOR IMAGE PROCESSING

CROSS REFERENCE TO RELATED APPLICATION

This application is a 371 of PCT/JP2014/058725 filed on Mar. 27, 2014, application which is incorporated herein by reference.

TECHNICAL FIELD

The present invention relates to an image processing device and an image processing program, and specifically relates to image processing for pathological diagnosis.

BACKGROUND ART

In recent years, with the spread of therapy using molecular target drugs based mainly on antibody drugs, the necessity of quantitating biological substances (for example, antigens) in the cell of the observation target has been increasing for sore efficient design of the molecular target drugs. For confirming the presence of a biological substance, a method of organization analysis is known on the basis of the binding of a biological substance and the fluorescent substance bonded with biological substance recognition site which bind the biological substance (for example, antibodies).

For example, according to the technique described in Patent Document 1, the expression level of a biological substance on the cell membrane is evaluated by staining cell membrane with a certain kind of fluorescent substance, staining a biological substance with another kind of fluorescent substance, and counting the number of fluorescent bright points which reflect the fluorescent substance on the cell membrane (see paragraphs 0012 to 0013, 0060 to 0066, 0107, etc.). However, the technique including a special step of staining the cell membrane as in Patent Document 1 takes labor, compared to the common method of organization analysis in which hematoxylin staining (H staining) or hematoxylin and eosin staining (HE staining) of a tissue slice is performed.

In contrast, according to the technique described in Patent Document 2, the expression level of a biological substance is evaluated on the basis of HE staining of a tissue slice (see paragraphs 0019, 0029, 0085, etc.).

SUMMARY OF INVENTION

Problems to be Solved by the Invention

However, according to the technique described in Patent Document 2, as shown in FIG. 18A, the estimated cell region 210 is a circular region of a prescribed distance from a centroid of the cell nucleus 202 in the cell 200 and the fluorescent bright points (204a, 204c, 224a, and 224b) are specified in the cell region 210. Accordingly, the fluorescent bright points 224a and 224b may be assigned to the cell (incorrect cell) 200, which is different from and neighbors the correct cell 220 containing the cell nucleus 222f to which the fluorescent bright points 224a and 224b should really be assigned.

On the contrary, in observing a tissue slice placed on a microscope slide after HE staining, as shown in FIG. 19A, the size of the cell nucleus 232 and 242 are different according to the different cutting position of cells 230 and 240. Accordingly, as shown in FIG. 19B, the fluorescent bright point 244 may be assigned to the cell (incorrect cell) 230, which is different from and neighbors the correct cell 240 containing the cell nucleus 242, to which the fluorescent bright point 244 should really be assigned.

Given the above, a main object of the present invention is to provide an image processing device and an image processing program capable of assigning the fluorescent bright point to the correct cell accurately.

Means for Solving Problems

According to an aspect of the present invention for solving the above-described problems, there is provided an image processing device including:
an input unit to input a bright field image of a tissue slice in which a cell nucleus is stained and a flourescent image of the tissue slice in which a specific biological substance is stained with a fluorescent staining reagent;
a first extracting unit to extract a cell nucleus from the cell nucleus image;
a second extracting unit to extract a fluorescent bright point from the fluorescent image; and
an assigning unit to specify a cell nucleus to which the fluorescent bright point is assigned on the basis of a distance between the cell nucleus and the fluorescent bright point and to assign the fluorescent bright point to the cell nucleus.

According to another aspect of the present invention, there is provided an image processing program for controlling a computer to function as:
an input unit to input a bright field image of a tissue slice in which a cell nucleus is stained and a fluorescent image of the tissue slice in which a specific biological substance is stained with fluorescent staining reagent;
a first extracting unit to extract a cell nucleus from the cell nucleus image;
a second extracting unit to extract a fluorescent bright point from the fluorescent image; and
an assigning unit to specify a cell nucleus to which the fluorescent bright point is assigned on the basis of a distance between the cell nucleus and the fluorescent bright point and to assign the fluorescent bright point to the cell nucleus.

Effects of the Invention

According to the present invention, it is possible to assign the fluorescent bright point to the cell nucleus accurately, because the cell nucleus with which the fluorescent bright point is assigned is specified on the basis of the actual distance between the cell nucleus and the fluorescent bright point.

BRIEF DESCRIPTION OF DRAWINGS

FIG. 11 is a flowchart schematically showing a flow of image analysis processing in the third embodiment.

FIG. 17 is a flowchart showing a modified example of image analysis processing in the first to fourth embodiments.

EMBODIMENT FOR CARRYING OUT THE INVENTION

Hereinafter, preferred embodiments of the present invention are described with reference to the drawings.
[First Embodiment]
<Configuration of Pathological Diagnosis Assistance System 10>

Figure 1:
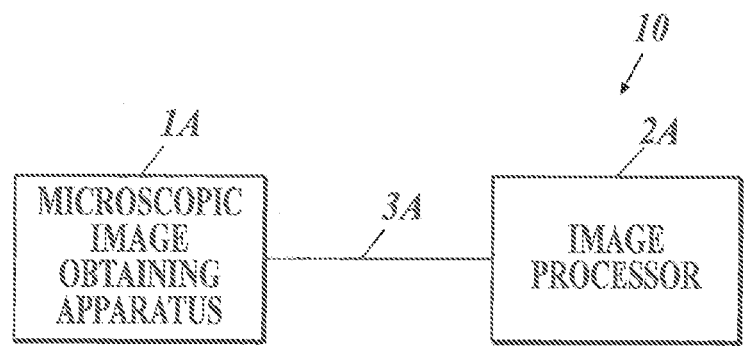
FIG. 1 is a diagram schematically showing a configuration of a pathological diagnosis assistance system.

FIG. 1 shows an example of an entire configuration of a pathological diagnosis assistance system 10.

The pathological diagnostic assistance system 10 obtains a microscopic image of a tissue slice of a human body stained with a predetermined staining reagent and outputs a feature amount quantitatively expressing a specific biological substance in the tissue slice of the observation target by analyzing the obtained microscopic image.

As shown in FIG. 1, the pathological diagnosis assistance system 10 includes a microscopic image obtaining apparatus 1A and an image processor 2A connected to each other through an interface such as a cable 3A so as to be able to transmit and receive data.

The connecting system of the microscopic image obtaining apparatus 1A and the image processor 2A is not particularly limited. For example, the microscopic image obtaining apparatus 1A and the image processor 2A can be connected by a LAN (Local Area Network) or can foe connected wirelessly.

The microscopic image obtaining apparatus 1A is a well-known optical microscope with a camera. The microscopic image obtaining apparatus 1A obtains the microscopic image of the tissue slice placed on the slide on a slide fixing stage, and transmits the image to the image processor 2A.

The microscopic image obtaining apparatus 1A includes an irradiating unit, an image forming unit, an imaging unit, a communication I/F, etc. The irradiating unit includes a light source, filter, etc., and irradiates the tissue slice placed on the slide on the slide fixing stage with light. The image forming unit includes an ocular lens, an object lens, etc., and forms an image of transmitted light, reflected light, or fluorescence light from the tissue slice on the slide due to the irradiated light. The imaging unit is a camera provided in a microscope which includes a CCD (Charge Coupled Device) sensor, etc., and images an image formed en an image forming face by the image forming unit to generate digital image data of the microscopic image. The communication I/F transmits the generated image data of the microscopic image to the image processor 2A.

The microscopic image obtaining apparatus 1A includes a bright field unit combining the irradiating unit and the image forming unit suitable for bright field observation and a fluorescent unit combining the irradiating unit and the image forming unit suitable for fluorescent observation. The bright field/fluorescence can be switched by switching the units.

The microscopic image obtaining apparatus 1A is not limited to a microscope with a camera. For example, a virtual microscope slide creating apparatus which scans a slide on a slide fixing stage of a microscope and obtains a microscopic image of the entire tissue slice can be used (for example, see Japanese Patent Application Laid-Open Publication No. 2002-514319). According to the virtual microscope slide creating apparatus, image data with which the entire image of the tissue slice on the slide can be viewed at once on the display section can be obtained.

The image processor 2A analyzes the microscopic image transmitted from the microscopic image obtaining apparatus 1A and calculates the distribution of a specific biological substance in the tissue slice of the observation target.

Figure 2:
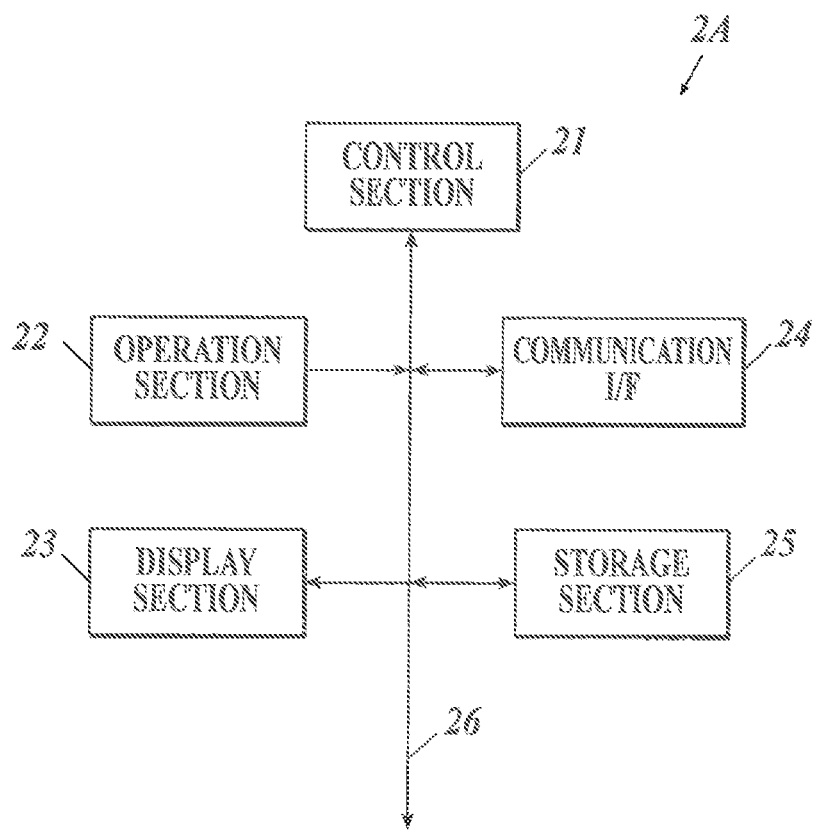
FIG. 2 is a block diagram schematically showing a functional configuration of an image processing device.

FIG. 2 shows an example of a functional configuration of the image processor 3A.

As shown in FIG. 2, the image processor 2A includes a control section 21, an operation section 22, a display section 23, a communication I/F 24, a storage section 25, and the like, and each section is connected through a bus 26.

The control section 21 includes a CPU (Central Processing Unit), a RAM (Random Access Memory), and the like, performs various processing in coordination with various programs stored in the storage section 25, and collectively controls the operation of the image processor 2A.

For example, the control section 21 performs image analysis processing (see FIG. 3) in coordination with a program stored in the storage section 25, and realizes functions as a first extracting unit, a second extracting unit, an assigning unit, and an excluding unit.

The operating section 22 includes a keyboard provided with character input keys, numeric input keys, and various function keys and a pointing device such as a mouse, and outputs depression signals of the pressed keys of the keyboard and operation signals of the mouse as the input signal to the control section 21.

The display section 23 includes a monitor such as a CRT (Cathode Ray Tube), an LCD (Liquid Crystal Display), etc., and displays various screens according to an instruction of a display signal input from the control section 21.

The communication I/F 24 is an interface for transmitting and receiving data with external devices such as the microscopic image obtaining apparatus 1A. The communication I/F 24 functions as the input unit of a bright field image and a fluorescent image.

The storage section 25 includes, for example, an HDD (Hard Disk Drive), a nonvolatile semiconductor memory, etc. The storage section 25 stores various programs and various pieces of data as described above.

Other than the above, the image processor 2A can include a LAN adaptor, a router, etc., and can be connected to external devices through a communication network such as a LAN.

The image processor 2A of the present embodiment analyzes the bright field image and the fluorescent image transmitted from the microscopic image obtaining apparatus 1A.

"A bright field image" is a microscopic image obtained by forming an enlarged image of a tissue slice stained with a reagent for hematoxylin stain (H staining reagent) or a reagent for hematoxylin-eosin stain (HE staining reagent) in a bright field in the microscopic image obtaining apparatus 1A, and capturing the image. The bright field image is a cell shape image showing a shape of cells in the tissue slice. Hematoxylin (H) is a blue purple dye and stains the cell nucleus, bone tissue, a portion of cartilage tissue, serous fluid component etc. (basophilic tissue, etc.). Eosin (E) is a red to pink dye and stains cytoplasm, connective tissue of soft tissue, red blood cell, fibrin, endocrine granule, etc. (eosinophilic tissue, etc.).

"A fluorescent image" is a microscopic image obtained by forming an enlarged image of the fluorescence emitted from the tissue slice stained with a fluorescent staining reagent by irradiation with excitation light having a predetermined wavelength in the microscopic image obtaining apparatus 1A, and capturing the image.

"A fluorescent staining reagent" is a staining reagent including fluorescent substance included nanoparticles bonded with a biological substance recognition site which specifically bonds and/or react with a specific biological substance. "A fluorescent substance included nanoparticle" is a nanoparticle including fluorescent substances.

The fluorescence which appears in the fluorescent image is emitted from the excited fluorescent substance included nanoparticle (fluorescent substances) in the fluorescent staining reagent, and shows expression of the specific biological substance corresponding to the biological substance recognition site in the tissue slice.

<Fluorescent Staining Reagent and Staining Method>

A fluorescent staining reagent and a staining method of a tissue slice using the fluorescent staining reagent is described.

(1) Fluorescent Substance

Examples of the fluorescent substance used in the fluorescent staining reagent include fluorescent organic dye and quantum dot (semiconductor particle). Preferably, the substance shows an emission of visible rays to near infrared rays having a wavelength within the range of 400 to 1100 nm when excited by ultraviolet rays to near infrared rays having a wavelength within the range of 200 to 700 nm.

Examples of fluorescent organic dye include, fluorescein type dye molecule, rhodamine type dye molecule, Alexa Fluor (manufactured by Invitrogen Corporation) type dye molecule, BODIPY (manufactured by Invitrogen Corporation) type dye molecule, cascade type dye molecule, coumarin type dye molecule, eosin type dye molecule, NBD type dye molecule, pyrene type dye molecule, Texas Red type dye molecule, cyanine type dye molecule, and the like.

Specific examples include, 5-carboxy-fluorescein, 6-carboxy-fluorescein, 5,6-dicarboxy-fluorescein; 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 60, tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 534, Alexa Fluor 610, Alexa Fluor 633, Alexa Fluor 835, Alexa Fluor 647, Alexa Fluor 660, Alexa Fluor 680, Alexa Fluor 700, Alexa Fluor 750, BODIPY FL, BODIPY TMR, BODIPY 433/503, BODIPY 530/550, BODIPY 558/568, BODIPY 564/570, BODIPY 576/589, BODIPY 581/591, BODIPY 630/650, BODIPY 650/665 (the above, manufactured by Invitrogen Corporation), methoxycoumalin, eosin, NBD, pyrene, Cy5, Cy5.5, Cy7, and the like. These fluorescent organic dyes can be used alone or by mixing a plurality of types.

Examples of quantum dots which can be used include quantum dots including the following as the component, II-VI compounds, III-V compounds, or IV element (also called, "XI-VI quantum dot", "III-V quantum dot", or "IV quantum dot", respectively). These quantum dots also can be used alone or by mixing a plurality of types.

Specific examples include, but are not limited to, CdSe, CdS, CdTe, ZnSe, ZnS, ZnTe, InP, InN, InAs, InGaP, GaP, GaAs, Si, and Ge.

A quantum dot having the above quantum dot as the core and a shell provided on the core can also be used. As a method of expressing the quantum dot including a shell in the following, a quantum dot having CdSe as the core and ZnS as the shell is expressed as CdSe/ZnS.

Examples which can be used include, but are not limited to, CdSe/ZnS, CdS/ZnS, InP/ZnS, InGaP/ZnS, Si/SiO$_2$, Si/ZnS, Ge/GeO$_2$, Ge/ZnS, etc.

The quantum dot in which the surface is processed with organic polymer, etc. can be used as necessary. Examples include CdSe/ZnS with surface carboxy group (manufactured by Invitrogen Corporation), CdSe/ZnS with surface amino group (manufactured by Invitrogen Corporation), and the like.

(2) Fluorescent Substance Included Nanoparticle

"A fluorescent substance included nanoparticle" is a nanoparticle including fluorescent substances as described above. More specifically, it is a nanoparticle with fluorescent substances dispersed inside, and the fluorescent substances and the nanoparticle itself can be chemically bonded or not bonded.

The material composing the nanoparticle is not particularly limited and examples include silica, polystyrene, polyactate, melamine, and the like.

The fluorescent substance included nanoparticle can be made by well-known methods.

For example, a silica nanoparticle including fluorescent organic dye can be synthesized by referring to synthesizing an FTIC included silica particle as described in Langmuir volume 8, page 2921 (1992). Various fluorescent organic dye included silica nanoparticles can be synthesized using a desired fluorescent organic dye instead of FITC.

The silica nanoparticle including the quantum dot can be synthesized by referring to synthesizing of the CdTe included silica nanoparticle as described in Mew Journal of Chemistry, Volume 33, page 561 (2003).

The polystyrene nanoparticle including the fluorescent organic dye can be made using the copolymerization method using the organic dye including polymerizable functional group as described in U.S. Pat. No. 4,326,008 (1982), and impregnating method of the fluorescent organic dye to the polystyrene nanoparticle as described in U.S. Pat. No. 5,326,632 (1992).

The polymer nanoparticle including the quantum dot can be made using the impregnating method of the quantum dot to the polystyrene nanoparticle as described in Nature Biotechnology Volume 19, page 631 (2001).

The average particle diameter of the fluorescent substance included nanoparticle is not particularly limited, and preferably, the fluorescent substance included nanoparticle with an average particle diameter with about 30 to 300 nm can be used. The coefficient of variation (=(standard deviation/average value)×100%) showing the variety of the particle diameter is not particularly limited, and preferably, the value is 20% or less.

The electronic microscope picture is captured using the scanning electron microscope (SEM), and the cross sectional area of a sufficient number of particles is measured. The diameter of the circle when each measured value is to be the area of the circle is obtained as the particle diameter. In the present embodiment, the average particle diameter is to be a calculated average of the particle diameter of 1000 particles. The coefficient of variation is also to be a value calculated from the particle diameter distribution of 1000 particles.

(3) Bonding of the Biological Substance Recognition Site and Fluorescent Substance Included Nanoparticle "A biological substance recognition site" is a site which specifically bonds and/or reacts with a specific biological substance.

The specific biological substance is not particularly limited as long as there is a substance which specifically bonds with the specific biological substance. Representative examples include protein (peptide), nucleic acid (oligonucleotide, polynucleotide), and the like.

Therefore, examples of the biological substance recognition site include antibody which recognizes the protein as antigen, other protein which specifically bonds with the protein, nucleic acid including a base sequence which hybridizes with the nucleic acid, and the like.

Specific examples of the biological substance recognition site include anti-HER2 antibody which specifically bonds with the HER2 which is a protein on the surface of the cell, anti-ER antibody which specifically bonds with the estrogen receptor (ER) in the cell nucleus, anti-actin antibody which specifically bonds with the actin forming the cytoskeleton, and the like.

Among the above, anti-HER2 antibody and anti-ER antibody bonded to the fluorescent substance included nanoparticle (fluorescent staining reagent) are preferable because they can be used for selecting drug administration to treat breast cancer.

The form of bonding between the biological substance recognition site and the fluorescent substance included nanoparticle is not particularly limited, and examples include, covalent bond, ionic bond, hydrogen bond, coordinate bond, physical adsorption, chemical adsorption, and the like. Bonding with strong bonding force such as covalent bond is preferable for the stability of bonding.

There can be an organic molecule which connects the biological substance recognition site with the fluorescent substance included nanoparticle. For example, in order to suppress non-specific absorption with the biological substance, a polyethyleneglycol chain, such as SM (PEG) 12 manufactured by Thermo Scientific, can be used.

When the biological substance recognition site is bonded to the fluorescent substance included silica nanoparticle, the same process can be applied whether the fluorescent substance is the fluorescent organic dye or the quantum dot.

For example, a silane coupling agent which is a compound widely used for bonding inorganic material and organic material can be used. The silane coupling agent is a compound including an alkoxysilyl group providing a silanol group with hydrolysis in one end of the molecule and a functional group such as carboxy group, amino group, epoxy group, aldehyde group, etc. in the other end, and bonds with the inorganic material through an oxygen atom of the silanol group.

Specific examples include, mercaptopropyl triethoxysilane, glycidoxypropyl triethoxysilane, aminopropyl triethoxysilane, silane coupling agent including polyethylene glycol chain (for example, FES-silane no. SIM6492.7 manufactured by Gelest Inc.), and the like.

When the silane coupling agent can be used, two or more types can be used together.

Well-known methods can be used as the reaction method between the fluorescent organic dye included silica nanoparticle and the silane coupling agent.

For example, the obtained fluorescent organic dye included silica nanoparticle can be dispersed in pure water, the aminopropyl triethoxysilane can be added, and the above can be reacted at room temperature for 12 hours. After the reaction ends, by centrifugal separation or filtration, it is possible to obtain a fluorescent organic dye included silica nanoparticle having a surface modified with the aminopropyl group. Next, the amino group is reacted with the carboxy group in the antibody so that the antibody can bond with the fluorescent organic dye included silica nanoparticle through amide bond. According to necessity, condensing agent such as EDC (1-Ethyl-3-[3-Dimethylaminopropyl]carbodiimide Hydrochloride: manufactured by Pierce (Registered Trademark)) can also be used.

According to necessity, a linker compound including a portion which can directly bond with the fluorescent organic dye included silica nanoparticle modified with the organic molecule and a portion which can bond with the molecular target substance can be used. For example, when sulfo-SMCC (Sulfosuccinimidyl 4[N-maleimidomethyl]-cyclohexane-1-carboxylate; manufactured by Pierce) which has a portion which selectively reacts with the amino group and a portion which selectively reacts with the mercapto group is used, the amino group of the fluorescent organic dye included silica nanoparticle modified with aminopropyl triethoxysilane and the mercapto group in the antibody are bonded, and with this, the fluorescent organic dye included silica nanoparticle bonded with the antibody is made.

When the biological substance recognition site is bonded to the fluorescent substance included polystyrene nanoparticle, the same process as the quantum dot can be applied whether the fluorescent substance is the fluorescent organic dye or the quantum dot. In other words, by impregnating the fluorescent organic dye and the quantum dot in the polystyrene nanoparticle with the functional group such as the amino group, etc., it is possible to obtain the fluorescent substance included polystyrene nanoparticle with the functional group, and then by using the EDC or the sulfo-SMCC, the fluorescent substance included polystyrene nanoparticle bonded with the antibody is made.

Examples of biological substance recognition site include the following antibody which recognizes the specific antigen, M. actin, M.S. actin, S.M. actin, ACTH, Alk-1, α1-antichymotrypsin, α1-antitrypsin, AFP, bcl-2, bcl-6, β-catenin, BCA 225, CA19-9, CA125, calcitonin, calretinin, CD1a, CD3, CD4, CD5, CD8, CD10, CD15, CD20, CD21, CD23, CD30, CD31, CD34, CD43, CD45, CD45R, CD56, CD57, CD61, CD68, CD79a, "CD99, MIC2", CD138, chromogranin, C-KIT, c-MET, collagen type IV, Cox-2, cyclin D1, keratin, cytokeratin (high molecular mass), pankeratin, pankeratin, cytokeratin 5/6, cytokeratin 7, cytokeratin 8, cytokeratin 8/18, cytokeratin 14, cytokeratin 19, cytokeratin 20, CMV, E-cadherin, EGFR, ER, EMA, EBV, VIII factor related antigen, fassin, FSH, galectin-3, gastrin, GFAP, glucagon, glycophorin A, granzyme B, hCG, hGH, *Helicobacter pyroli*, HBc antigen, HBs antigen, hepatocyte specific antigen, HER2, HSV-I, HSV-II, HHV-8, IgA, IgG, IgM, IGF-1R, inhibin, insulin, kappa L chain, Ki67, lambda D chain, LH, lysozyme, macrophage, melan A, MLH-1, MSH-2, myeloperoxidase, myogenin, myoglobin, myosin, neurofilament, NSE, p27 (Kip1), p53, p53, p63, PAX 5, PLAP, pneumocystis calini, podoplanin (D2-40), PGR, prolactin, PSA, prostatic acid phosphatase, Renal Cell Carcinoma, S100, somatostatin, spectrin, synaptophysin, TAG-72, TdT, thyroglobulin, TSH, TTF-1, TRAcP, tryptase, villin, vimentin, WT1, Zap-70, and the like.

(4) Staining Method

The staining method described below is not limited to a pathological tissue slice, and can be applied to cultured cells.

The method of creating the tissue slice is not particularly limited, and the slice which is made by well-known methods can be need.

(4.1) Removing Paraffin

A tissue slice is immersed in a container with xylene, and paraffin is removed. The temperature is not particularly limited, and the processing can be performed at room temperature. Preferably, the immersing time is 3 minutes or more to 30 minutes or less. The xylene can be changed during the immersion as necessary.

Next, the tissue slice is immersed in a container with ethanol, and the xylene is removed. The temperature is not particularly limited, and the processing can be performed at room temperature. Preferably, the immersing time is 3 minutes or more to 30 minutes or less. The ethanol can be changed during the immersion as necessary.

Next, the tissue slice is immersed in a container with water, and the ethanol is removed. The temperature is not particularly limited, and the processing can be performed at room temperature. Preferably, the immersing time is 3 minutes or more to 30 minutes or less. The water can be changed during the immersion as necessary.

(4.2) Activating Processing

Activating processing of the biological substance in the tissue slice is performed according to well-known methods.

Although the activating conditions are not specifically set, examples of activating liquid that can be used include, 0.01M citric acid buffered solution (pH 6.0), 1 mM EDTA solution (pH 8.0), 5% urea, 0.1M tris-hydrochloric acid buffered solution. Examples of the heating device that can be used include autoclave, microwave, pressure pan, water bath, etc. The temperature is not particularly limited, and the processing can be performed at room temperature. The processing can be performed at a temperature of 50 to 130° C. and the amount of time that the processing is performed can be 5 to 30 minutes.

Next, the tissue slice after activating processing is immersed in the container with PBS (Phosphate Buffered Saline), and cleaning is performed. The temperature is not limited, and the processing can be performed at room temperature. Preferably, the immersing time is 3 minutes or more to 30 minutes or less. The PBS can be changed during the immersion as necessary.

(4.3) Stain Using Fluorescent Staining Reagent

The PBS dispersion liquid of the fluorescent staining reagent is placed on the tissue slice and reacted with the biological substance in the tissue slice.

By changing the biological substance recognition site in the fluorescent staining reagent, staining can be applied to various biological substances. When the fluorescent substance included nanoparticle bonded with plural types of biological substance recognition sites is used as the fluorescent staining reagent, the fluorescent substance included nanoparticle PBS dispersion liquid of each of the above can be mixed in advance, or the liquid can be sequentially placed on the tissue slice separately. The temperature is not particularly limited, and the processing can be performed at roots temperature. Preferably, the reacting time is 30 minutes or more to 24 hours or less.

Preferably, a well-known blocking agent such as BSA included in PBS is dropped before staining with the fluorescent staining reagent.

Next, the tissue slice after staining is immersed in the container with PBS, and the unreached fluorescent substance included nanoparticle is removed. The temperature is not particularly limited, and the processing can be performed at room temperature. Preferably, the immersing time is 3 minutes or more to 30 minutes or less. The PBS can be changed during the immersion as necessary. A cover glass is placed on the tissue slice to be sealed. A commercially available sealing agent can be used as necessary.

The HE staining with a HE staining reagent is performed before sealing with the cover glass.

(5) Obtaining Fluorescent Image

The microscopic image obtaining apparatus 1A is used on the stained tissue slice to obtain the microscopic image (fluorescent image) with a wide visual field. In the microscopic image obtaining apparatus 1A, the excitation light source and the fluorescence detecting optical filter are selected according to the absorption maximum wavelength and the fluorescent wavelength of the fluorescent substance used in the fluorescent staining reagent.

Preferably, the visual field of the fluorescent image is 3 mm$^2$ or more, more preferably 30 mm$^2$ or more, and even more preferably 300 mm$^2$ or more.

<Operation of Pathological Diagnosis Assistance System 10 (Including the Method of Image Processing)>

Below, the operation of obtaining the above described bright field image and the fluorescent image and performing analysis in the pathological diagnosis assistance system 10 is described.

The example of the observation target here is a tissue slice of a breast cancer tissue including HER2 protein as a specific biological substances.

First, the operator stains the tissue slice using two kinds of staining reagent, that is, a HE staining reagent and a fluorescent staining reagent (the fluorescent substance included nanoparticle bonded with anti-HER2 antibody).

Subsequently, the bright field image and the fluorescent image are obtained with the microscopic image obtaining apparatus 1A by steps (a1) to (a5).

(a1) The operator mounts the tissue slice stained with an HE staining reagent and a fluorescent staining reagent on a slide, and places the slide on a slide fixing stage of the microscopic image obtaining apparatus 1A.

(a2) The bright field unit is set, the capturing magnification and focus are adjusted, and the region of the observation target of the tissue slice is positioned in the visual field.

(a3) Capturing is performed with the cap tearing unit to generate the image data of the bright field image, and the image data is transmitted to the image processor 2A.

(a4) The unit is changed to the fluorescent unit.

(a5) Capturing is performed with the capturing unit without changing the visual field and the capturing magnification to generate the image data of the fluorescent image, and the image data is transmitted to the image processor 2A.

Subsequently, image analysis processing is performed on the basis of the bright field image and the fluorescent image in the image processor 2A.

Figure 3:
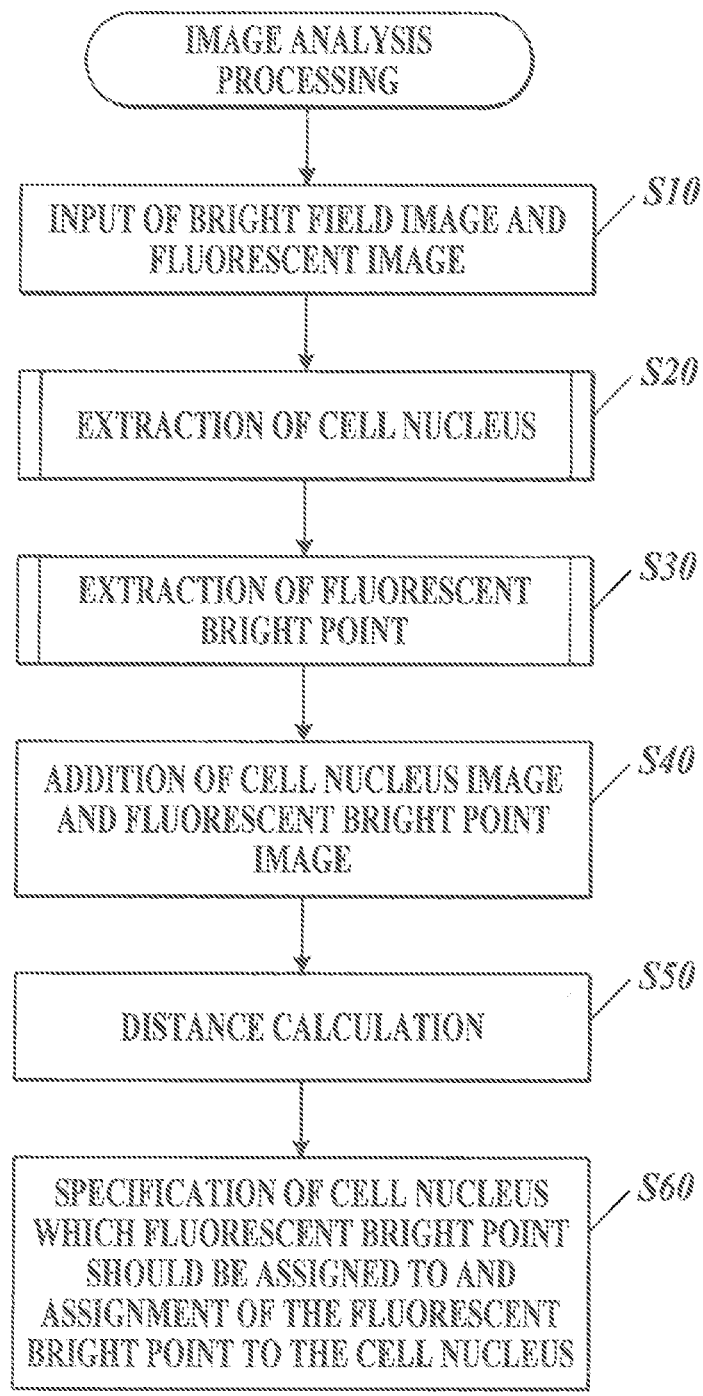
FIG. 3 is a flowchart schematically showing a flow of image analysis processing in the first embodiment.

FIG. 3 shows a flowchart of the image analysis processing in the image processor 2A.

The image analysis processing shown in FIG. 3 is performed by the control section 21 in coordination with the image processing program stored in the storage section 25. The control section 21 performs the processing as described below in accordance with the image processing program.

First, when the bright field image and the fluorescent image are input from the microscopic image obtaining apparatus 1A through the communication I/F 24 (step S10), the region of the cell nucleus is extracted from the bright field image (step S20).

Figure 4:
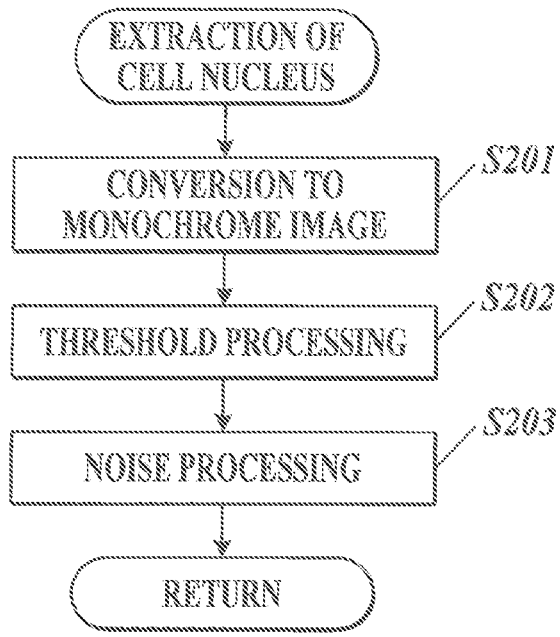
FIG. 4 is a flowchart schematically showing a flow of extracting a cell nucleus region.

In step S20, as shown in FIG. 4, the conversion of the bright field image to the monochrome image is performed (step S201), threshold processing is performed on the monochrome image using a predetermined threshold to binarize each value of the pixel (step S202), and noise processing is performed on the binary image (step S203).

Specifically, the noise processing can be performed by performing closing processing on the binary image. The closing processing is processing of performing dilation processing and then erosion processing by the same number of times. The dilation processing is processing of replacing the target pixel with a white pixel when any of the pixels within the range of n×n pixels (n is an integer of 2 or more) from the target pixel is white. The erosion processing is processing of replacing the target pixel with a black pixel when any of the pixels within the range of n×n pixels from the target pixel is black. Small regions such as noise can be removed by the closing processing.

After the processing of steps S201 to S203, an image with the cell nucleus extracted (cell nucleus image) can be obtained.

Subsequently, the control section 21 returns to the processings shown in FIG. 3 and extracts the fluorescent bright points from the fluorescent image (step S30).

Figure 5:
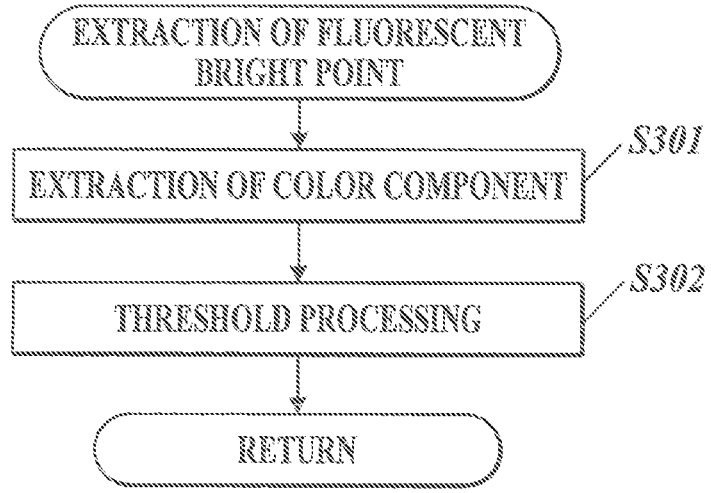
FIG. 5 is a flowchart schematically showing a flow of extracting a fluorescent bright point.

In Step S30, as shown in FIG. 5, a color component is extracted according to the wavelength of the fluorescent bright points from the fluorescent image (step S301) and threshold processing is performed on the fluorescent image from which the color component is extracted to obtain a binary image (step S302).

In step S301, when the emission wavelength of the fluorescent substance included nanoparticle is 550 nm, for example, only the fluorescent bright points having the wavelength are extracted as an image.

After the processing of steps S301 to S302, the image with the fluorescent bright points extracted (fluorescent bright point image) is obtained.

Before the threshold processing in step S302, noise removal processing can be performed to remove the autofluorescence of the cell, other components due to unnecessary signals, etc.

The order of steps S20 and S30 can be exchanged.

Subsequently, the control section 21 returns to the processings shown in FIG. 3 and performs addition processing of the cell nucleus image and the fluorescent bright point image, to overlap the cell nucleus image and the fluorescent bright point image (step S40).

Subsequently, in the overlapped images after addition processing, the distances between the cell nuclei and the fluorescent bright points are measured (step S50). On the basis of the distances, the cell nucleus to which each of the fluorescent bright point is assigned is specified and the fluorescent bright point is assigned to the cell nucleus (step S60).

Figure 6A:
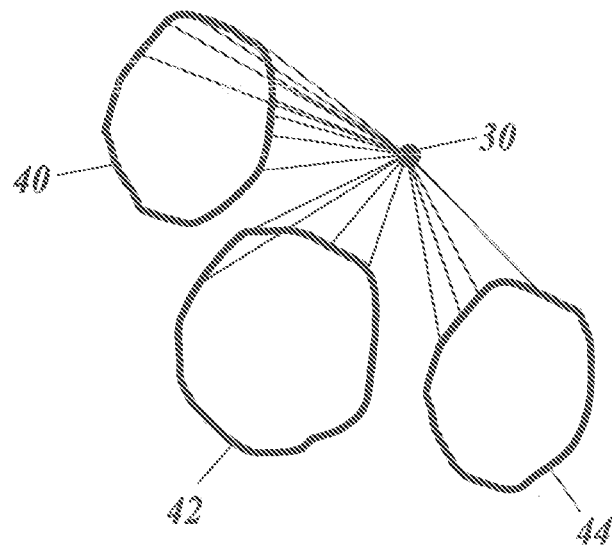
FIG. 6A is a diagram schematically illustrating the calculating of distances from surface of cell nuclei to a fluorescent bright point.

More specifically, in step S50, the distances are calculated from the fluorescent bright point 30 to the surface of the cell nuclei 40, 42, and 44, as shown in FIG. 6A. The calculation of the distances is conducted to all the pixels in the cell nuclei 40, 42, and 44.

Figure 6B:
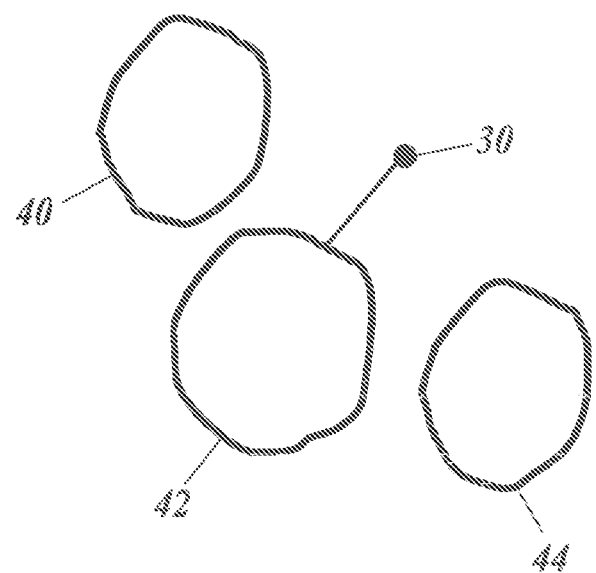
FIG. 6B is a diagram schematically showing a cell nucleus at the shortest distance from a fluorescent bright point.

In step S60, as shown in FIG. 6B, the shortest distance is determined among the distances from the fluorescent bright point 30 to the cell nuclei 40, 42, and 44. The cell nucleus 42 is specified as the cell nucleus nearest to the fluorescent bright point 30 and the fluorescent bright point 30 is assigned to the cell nucleus 42.

Figure 7:
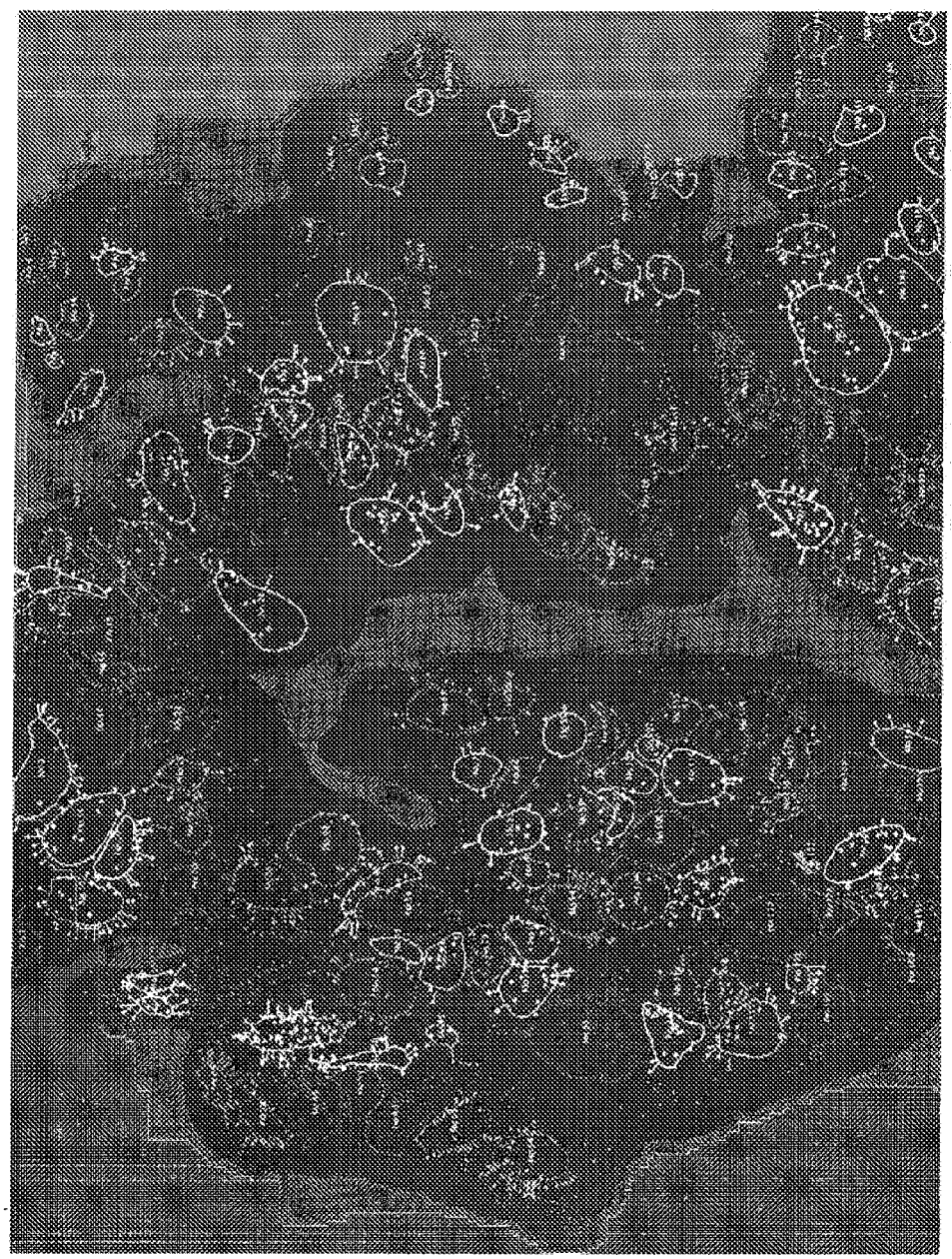
FIG. 7 is a diagram schematically showing fluorescent bright points assigned to cell nuclei.

FIG. 7 is a diagram showing an example of fluorescent bright points assigned to cell nuclei.

According to the first embodiment described above, it is possible to assign the fluorescent bright point with the correct cell accurately because the cell nucleus to which the fluorescent bright point is assigned is specified on the basis of the shortest distance actually calculated from the fluorescent bright point to the surface of the cell nucleus. This provides an accurate pathological diagnosis.

Figure 18A:
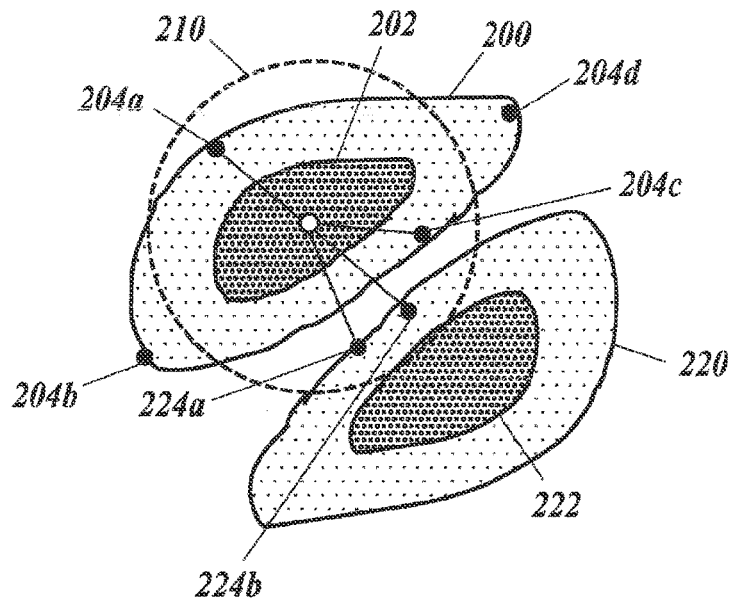
FIG. 18A is a diagram schematically illustrating a problem of a prior art.
Figure 18B:
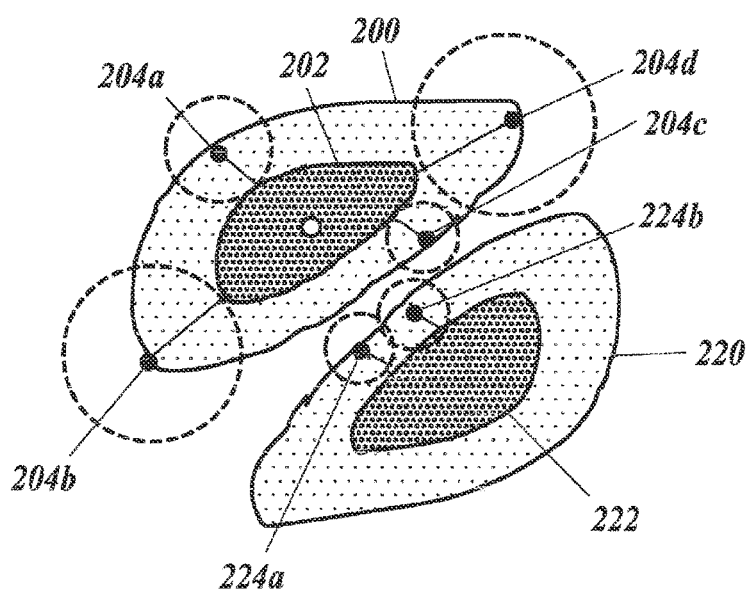
FIG. 18B is a diagram schematically comparing and illustrating a prior art and an embodiment of the present invention.

According to the technique described in Patent Document 2, the estimation of cell region 210 is necessary and the fluorescent bright points may be assigned to the incorrect cell when the estimated range of the cell region 210 is expanded too much as shown in FIG. 18A. In comparison with the technique described in Patent Document 2, the processing of estimating the cell region itself is unnecessary according to the first embodiment and the fluorescent bright points 204a to 204d and the fluorescent bright points 224a and 224b can be respectively assigned to the correct cells 200 and 220 as shown in FIG. 18B, preventing the fluorescent bright points 224a and 224b from being assigned to the incorrect cell 200.

Figure 19A:
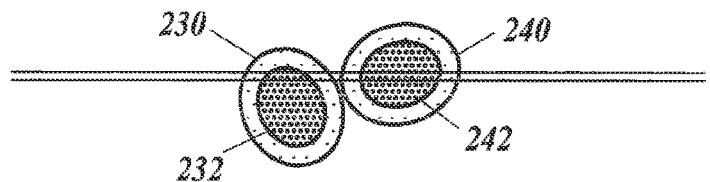
FIG. 19A is a diagram schematically illustrating a prior art.
Figure 19B:
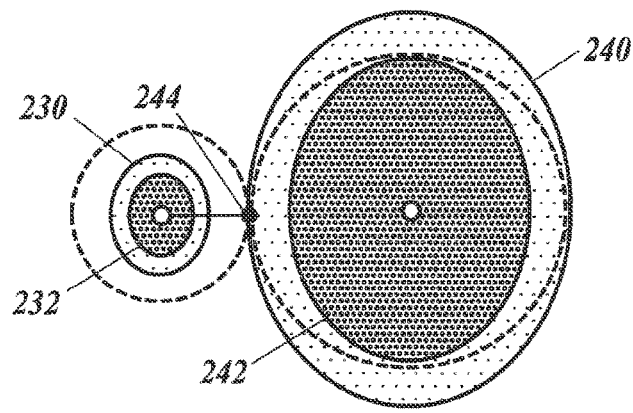
FIG. 19B is a diagram schematically illustrating a problem of a prior art.
Figure 19C:
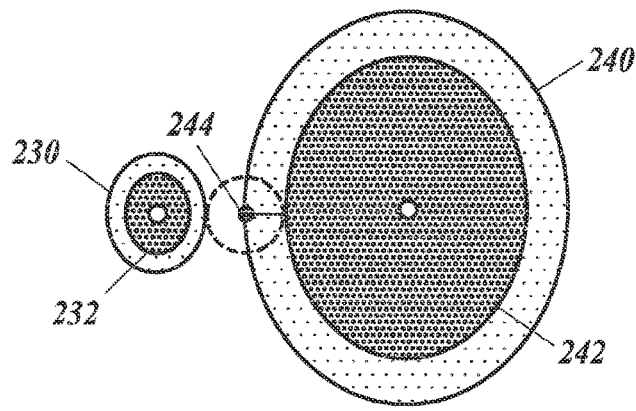
FIG. 19C is a diagram schematically comparing and illustrating a prior art and an embodiment of the present invention.

Furthermore, according to the technique described in Patent Document 2, as shown in FIG. 19B, the fluorescent bright point 244 may be assigned to the incorrect cell 230 due to the cross sections of cells 230 and 240. On the other hand, according to the first embodiment, as shown in FIG. 19C, the fluorescent bright point 244 can be assigned to the correct cell 240, regardless of the cross sections of cells 230 and 240.

[Second Embodiment]

The second embodiment is different from the first embodiment mainly in the following points, and is the same as the first embodiment in other points.

Figure 8:
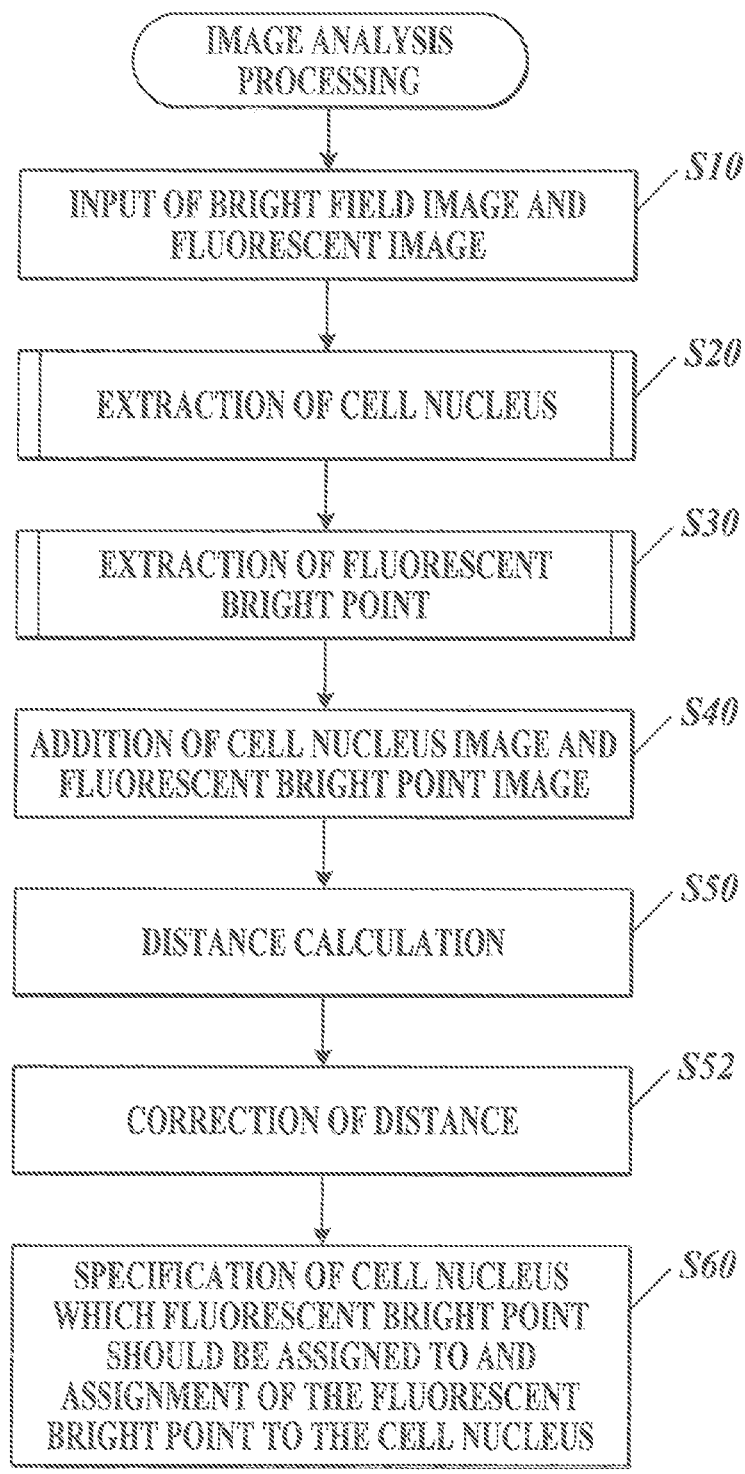
FIG. 8 is a flowchart schematically showing a flow of image analysis processing in the second embodiment.

As shown in FIG. 8, after step S50, the distance calculated in step S50 is corrected on the basis of the shape of cell nucleus (step S52).

Figure 9:
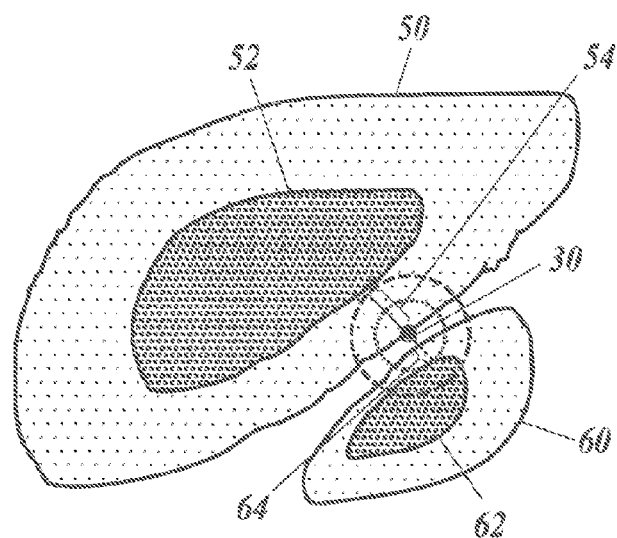
FIG. 9 is a diagram schematically illustrating correction of distances from surface of cell nuclei to a fluorescent bright point.

For example, as shown in FIG. 9, while the fluorescent bright point 30 should be assigned to the cell 50, the distance 64 from the fluorescent bright point 30 to the surface of the cell nucleus 62 in the cell 60 is sometimes shorter than the distance 54 from the fluorescent bright point 30 to the surface of the cell nucleus 52 in the cell 50.

In this case, in step S52, the area of the cell nucleus 52 and the area of the cell nucleus 62 are calculated and used for correcting the distance 54 and the distance 64.

More specifically, the distance 54 and the distance 64 are corrected according to the correction formulas (1) and (2).

$$\text{Distance } 54a = (\text{distance } 54)/\sqrt{(\text{area of cell nucleus } 52)} \quad (1)$$

$$\text{Distance } 64a = (\text{distance } 64)/\sqrt{(\text{area of cell nucleus } 62)} \quad (2)$$

According to the correction formulas (1) and (2), the size relation of the distance 54 and the distance 64 is reversed, by inverse proportion calculation based on the area of the cell nucleus 52 and the area of the cell nucleus 62.

As a result, in step S60, the fluorescent bright point 30 can be assigned to the cell nucleus 52, relating to the shorter distance of the distance 54a and the distance 64a.

Figure 10:
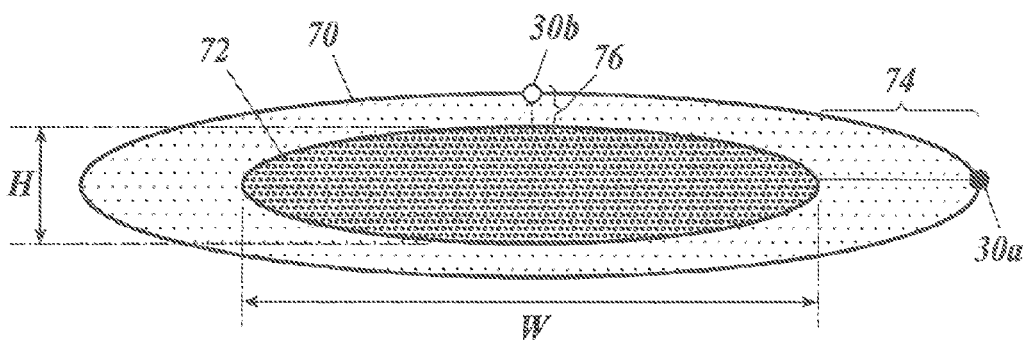
FIG. 10 is a diagram schematically illustrating correction of distances from surface of a cell nucleus to fluorescent bright points.

On the other hand, as shown in FIG. 10, the distance 74 from the fluorescent bright point 30a to the surface of the cell nucleus 72 is sometimes remarkably different from the distance 76 from the fluorescent bright point 30b to the surface of the cell nucleus 72, as a result of partial contractions or elongations of the cell 70 (the cell nucleus 72) due to the crush in preparing or in staining the tissue slice.

In this case, the distance 74 and the distance 76 are corrected in step S52, on the basis of the flatness of the cell nucleus 72 which is calculated from the width (W) and height (H) of the cell nucleus 72.

More specifically, the distance 74 and the distance 76 are corrected according to the correction formulas (3) and (4).

$$\text{Distance } 74a = (\text{distance } 74) \times ((\text{height } H)/(\text{width } W)) \quad (3)$$

$$\text{Distance } 76a = (\text{distance } 76) \times ((\text{width } W)/(\text{height } H)) \quad (4)$$

The distance 74a and the distance 76a calculated by the correction formulas (3) and (4) can be treated almost in the same scale, because the difference of the distance is reduced between the distance 74a and the distance 76a.

As a result, in step S60, both the fluorescent bright point 30a and the fluorescent bright point 30b can be determined to assign to the same cell nucleus 70 on the basis of the distance 74a and the distance 76a.

[Third Embodiment]

The third embodiment is different from the first embodiment mainly in the following points, and is the same as the first embodiment in other points.

As shown in FIG. 11, before step S50, a threshold is set for the distance between the cell nucleus and the fluorescent bright point (step S42) and the cell nuclei to which the fluorescent bright point is assigned is limited (step S44).

Figure 12A:
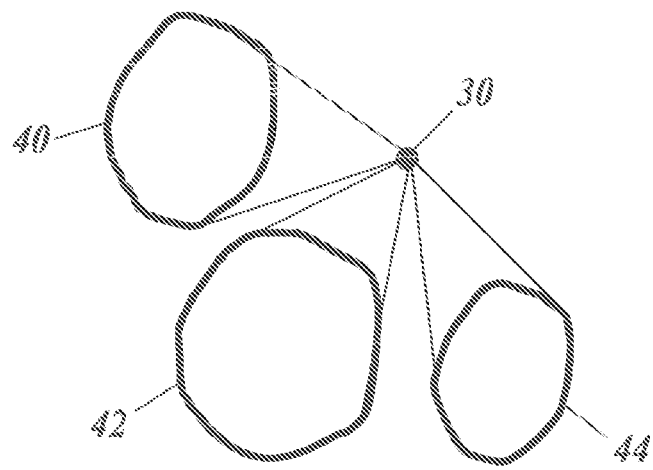
FIG. 12A is a diagram schematically illustrating a problem in calculating distances from surface of cell nuclei to a fluorescent bright point.

For example, as shown in FIG. 12A, the processing in step S50 may be delayed due to an enormous amount of distance calculation from the fluorescent bright point 30 to the surface of cell nuclei if the distance calculation from the fluorescent bright point 30 to the cell nuclei 40, 42, and 44 is conducted from the fluorescent bright point 30 to all the pixels in the cell nuclei including the cell nuclei 40, 42, and 44.

Figure 12B:
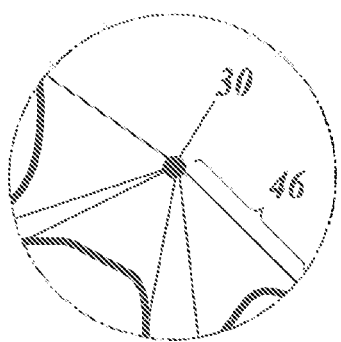
FIG. 12B is a diagram schematically illustrating setting of a threshold value of a distance from surface of cell nuclei to a fluorescent bright point.

In this case, in step S42, a threshold (radius distance 46) is set in order to define a predetermined circular range from the fluorescent bright point 30 as shown in FIG. 12B. In step S44, the cell nuclei targeted for distance calculation in step S50 is limited to the cell nuclei 40, 42, and 44, which are partially or wholly included within the radius distance 46. The cell nuclei 40, 42, and 44 are targeted for distance calculation in step S50.

Figure 12C:
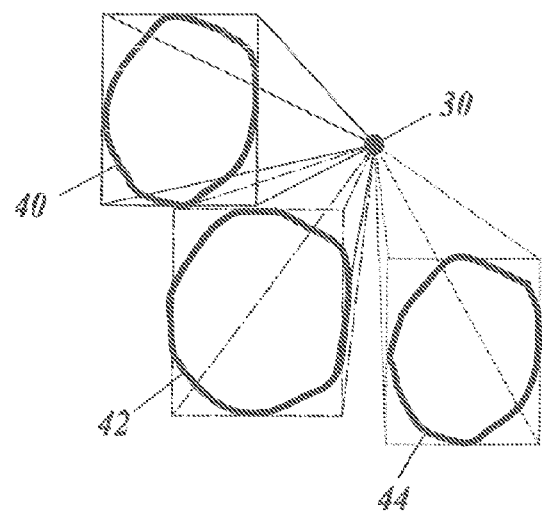
FIG. 12C is a diagram schematically illustrating setting of a threshold value of a distance from surface of cell nuclei to a fluorescent bright point.

Alternatively, in step S42, a rectangular frame including a cell nucleus can be assumed to set a threshold (total distance 48) for the total distance from each of the four vertexes of the frame to the fluorescent bright point. In step S44, as shown in FIG. 12C, the total distances regarding the cell nuclei 40, 42, and 44 can be calculated from each of the four vertexes of the frames including the cell nuclei 40, 42, and 44 respectively to the fluorescent bright point 30. The target cell nucleus for distance calculation in step S50 can be limited to the cell nucleus 44 having the total distance within the limited distance 48. The cell nucleus 44 can be determined as the target for distance calculation in step S50.

Particularly in step S44, while the rectangular frames respectively including the cell nuclei 40, 42, and 44 are assumed and the total distance is calculated from each of the four vertexes of the frame to the fluorescent bright point 30, the calculation is stopped when the total distance exceeded the limited distance 48. The cell nuclei 40 and 42 under calculation are then excluded from the target cell nuclei for distance calculation in step S50.

As a result, only the cell nuclei within a certain distance from the fluorescent bright point are determined as the target of distance calculation in step S50, and the distance calculation between the surface of the cell nuclei and the fluorescent bright point can be accelerated.

The radius distance 46 and the total distance 48, which are set as thresholds in step S42, can be properly set on the basis of the area of the cell nucleus, the area of the cell membrane, N/C ratio (Nuclear-cytoplasm ratio), etc.

Figure 13:
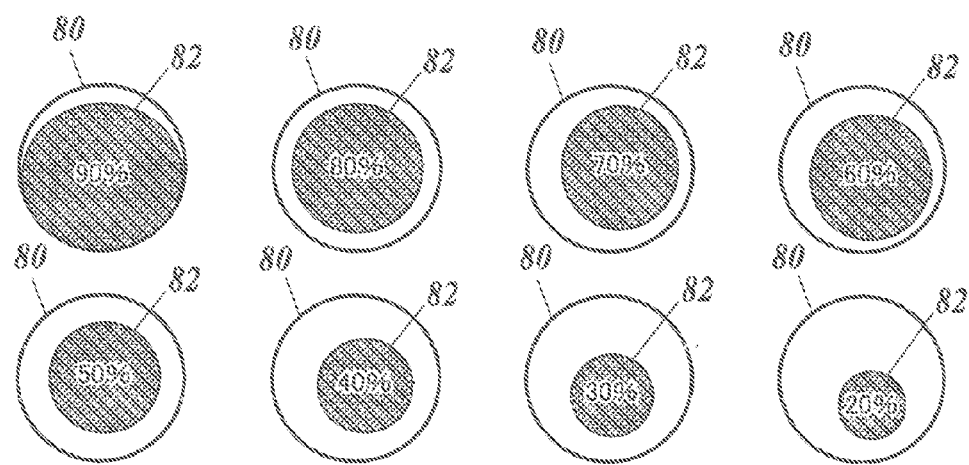
FIG. 13 is a diagram schematically showing N/C ratio of cells.

"An N/C ratio" is, as shown in FIG. 13, defined as the ratio of the area of the cell nucleus 82 to the area of the cytoplasm 80 and the range of its value depends on the kind of cell, the state of cell, etc.

The rectangular frame assumed in steps S42 and S44 can be replaced with a frame of any shape, as long as it can include a cell nucleus.

[Fourth Embodiment]

The fourth embodiment is different from the first embodiment mainly in the following points, and is the same as the first embodiment in other points.

Figure 14:
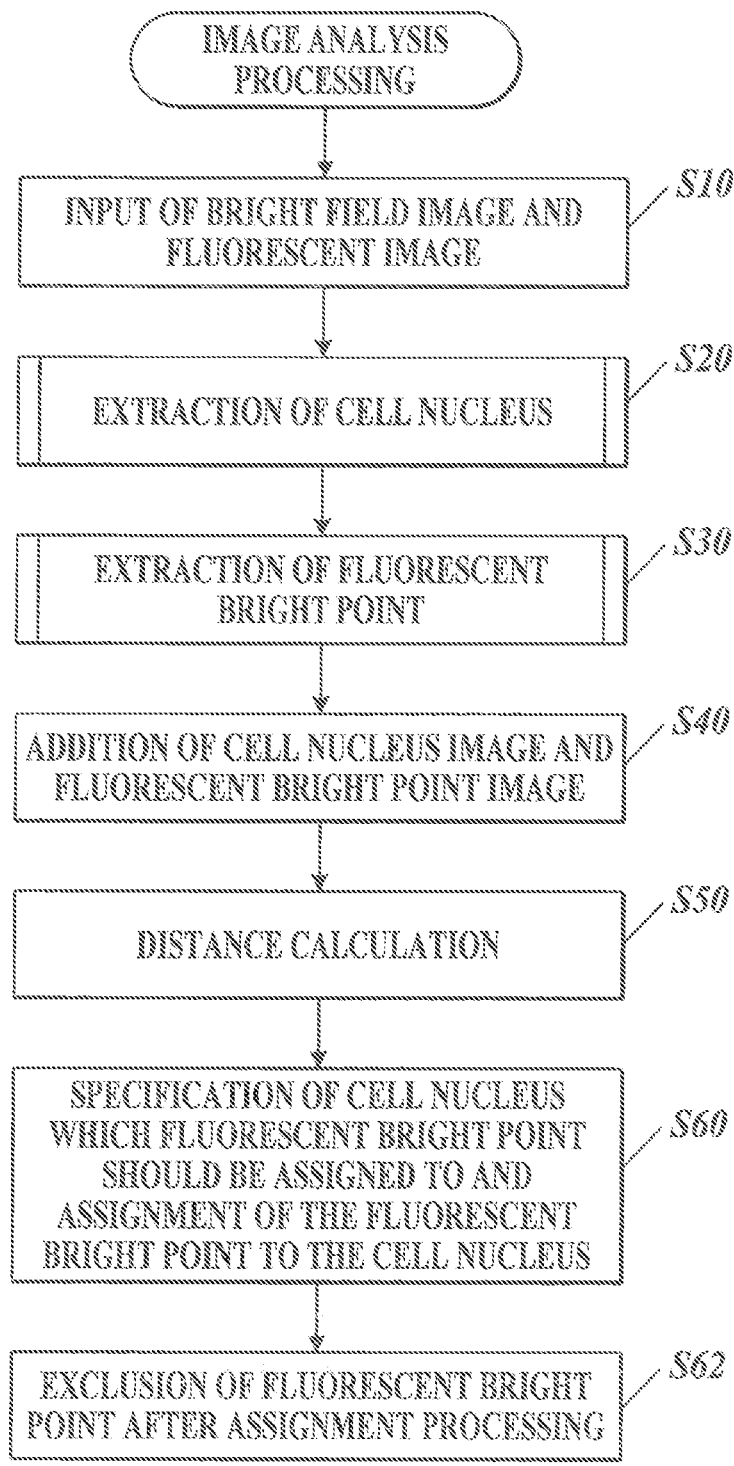
FIG. 14 is a flowchart schematically showing a flow of image analysis processing in the fourth embodiment.

As shown in FIG. 14, after step S50, the fluorescent bright points after assignment processing are excluded from the assigned fluorescent bright points (step S62).

Figure 15:
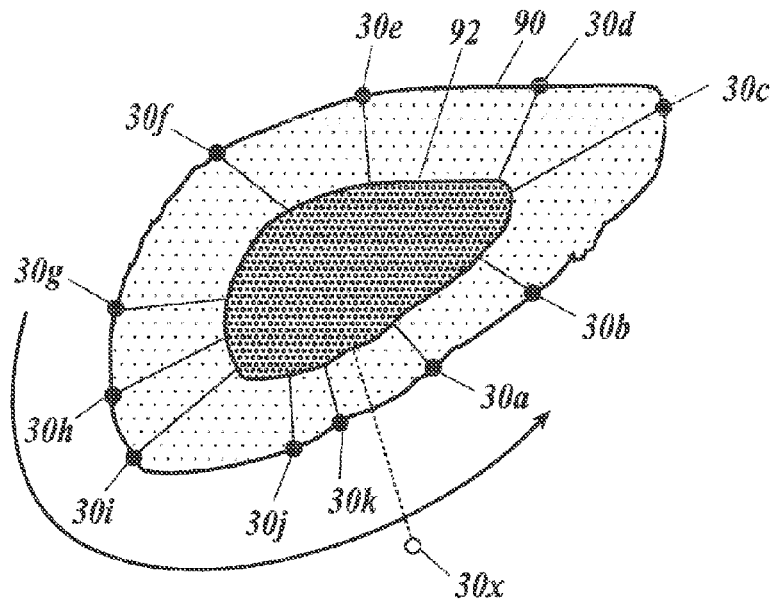
FIG. 15 is a diagram schematically illustrating exclusion of a fluorescent bright point from assigned fluorescent bright points.

For example, as shown in FIG. 15, the fluorescent bright point 30x which should be assigned to the cell other than the cell 30 may be incorrectly assigned to the cell nucleus 92 in the cell 90, while the fluorescent bright points 30a to 30k are correctly assigned to the cell nucleus 92 in the cell 90.

In this case, in step S62, as shown in FIG. 15, the average distance 104 is calculated from the surface of cell nucleus 92 to each of the fluorescent bright points 30a to 30k and 30x after assignment processing, and the fluorescent bright point 30x is excluded from the assigned fluorescent bright points because of the distance from the surface of cell nucleus 92 to the fluorescent bright point 30x remarkably longer than the average distance 104.

Alternatively, the straight lines connecting two of the fluorescent bright points 30a to 30k and 30x (that is, the lines from the fluorescent bright point 30a to 30b, from 30b to 30c, from 30c to . . . , . . . to 30k, from 30k to 30x, and from 30x to 30a) can be assumed. The inclinations or angles between the neighboring lines are calculated and compared sequentially following the arrangement order of the fluorescent bright points 30a, 30b, , . . . , 30k, 30x, and 30a. The fluorescent bright point 30x can be excluded from the assigned fluorescent bright points because of the sudden change of the value of inclinations or angles at the line including the fluorescent bright point 30x.

As a result, in step S62, the accuracy of assigning the fluorescent bright point to the cell nucleus is improved and the fluorescent bright point can be assigned to the correct cell more accurately.

Figure 16:
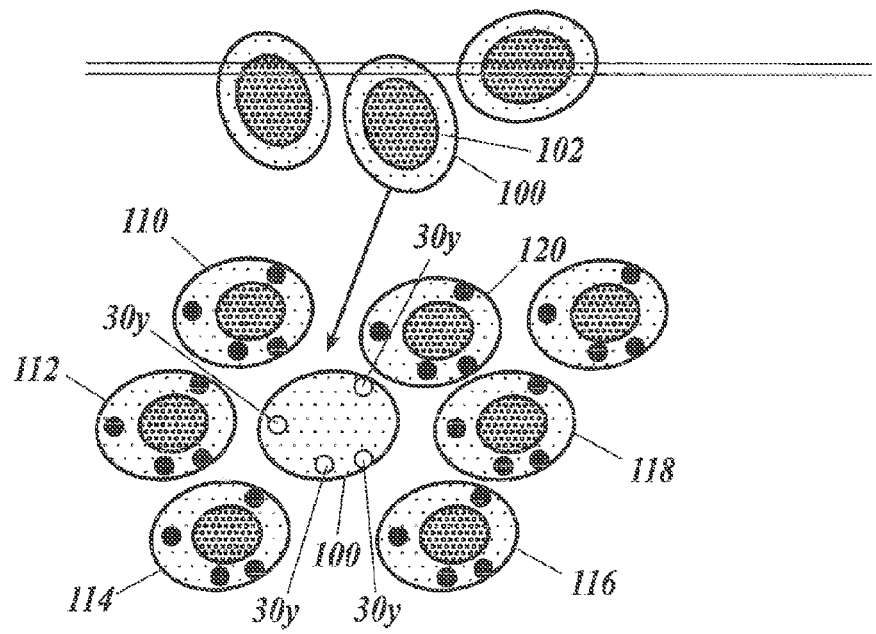
FIG. 16 is a diagram schematically illustrating exclusion of fluorescent bright points from assigned fluorescent bright points.

On the other hand, as shown in FIG. 16, when the cell nucleus 102 is not included in the cross section of cell 100, the fluorescent bright points 30y in cell 100 may be determined to assign not to the cell nucleus 102 but to any of the cells 110 to 120 other than cell 100.

In this case, the N/C ratio (see FIG. 13) is calculated for each of the cells 100 and 110 to 120, to which the fluorescent bright points are assigned in step S60. If the N/C ratio of cell 100 is smaller than a predetermined N/C ratio (for example, 70%), the fluorescent bright points 30y assigned to the cell 100 are excluded from the assigned fluorescent bright points.

Also in this case, in step S62, the accuracy of assigning the fluorescent bright point to the cell nucleus is improved and the fluorescent bright point can be determined to assign to the correct cell more accurately.

The descriptions of the first to fourth embodiments are suitable examples of the present invention, and the present invention is not limited to them.

For example, the first to fourth embodiments can be combined as shown in FIG. 17, and step S52 (second embodiment) after step S50, steps S42 and S44 (third embodiment) before step S50, and step S62 (fourth embodiment) after step S60 can be respectively performed in the image analysis processing.

Of coarse, any two or three of the first to fourth embodiments can be combined.

HER2 protein in breast cancer is described as the specific biological substance according to the first to fourth embodiments, however, the specific biological substance is not limited to the above. It is possible to provide the physician with the feature amount quantitatively showing the expression amount of the specific protein according to the type of lesion by changing the biological substance recognition site used for obtaining the fluorescent image according to the type of lesion (cancer) which is to be the target of diagnosis.

According to the first to fourth embodiments, a tissue slice of a human body is described as the object of the pathological diagnosis. The tissue slice includes tissue culture and can be replaced with separated cells from the tissue or cultured cells.

The above description discloses an example which uses an HDD, a semiconductor nonvolatile memory, or the like as the computer readable medium of the program of the present invention, however, the present invention is not limited to the above. A portable recording medium such as a CD-ROM, etc. can be applied as other computer readable media. A carrier wave can be applied as the medium which provides the data of the program of the present invention through a communication line.

Other than the above, the detailed configuration and the detailed operation of each device composing the pathological diagnosis assistance system 10 can be suitably changed within the scope of the present invention.

INDUSTRIAL APPLICABILITY

The present invention can be used in the field of image processing for pathological diagnosis.

REFERENCE NUMERALS 1A microscopic image obtaining apparatus
2A image processor
3A cable
10 pathological diagnosis assistance system
21 control section
22 operation section
23 display section
24 communication I/F
25 storage section
26 bus
30, 30a to 30k, 30x, and 30y fluorescent bright point
40, 42, and 44 cell nucleus
46 radius distance
50 cell
52 cell nucleus
54 distance
60 cell
62 cell nucleus
64 distance
70 cell
72 cell nucleus
74 and 76 distance
80 cytoplasm
82 cell nucleus
30 cell
92 cell nucleus
100 cell
102 cell nucleus
110, 112, 114, 116, 118, and 120 cell

The invention claimed is:

1. An image processing device comprising:
an input unit to input a bright field image of a tissue slice in which a cell nucleus is stained and a fluorescent image of the tissue slice in which a specific biological substance is stained with a fluorescent staining reagent;
a first extracting unit to extract a cell nucleus from the bright field image;
a second extracting unit to extract a fluorescent bright point from the fluorescent image;
an assigning unit to specify a cell nucleus to which the fluorescent bright point is assigned on the basis of a distance between the cell nucleus and the fluorescent bright point and to assign. the fluorescent bright point to the cell nucleus; and
an excluding unit to exclude a fluorescent bright point after assignment processing from the assigned fluorescent bright points on the basis of an average distance between a surface of the cell nucleus and the fluorescent bright point after assignment processing, inclination or angle between straight lines connecting the fluorescent bright points after assignment processing, or the N/C ratio of the cell to which the fluorescent bright point is assigned.

2. The image processing device of claim 1, wherein,
the assigning unit calculates a shortest distance between a surface of the cell nucleus and the fluorescent bright point and assigns the fluorescent bright, point to the cell nucleus at the shortest. distance.

3. The image processing device of claim 1, wherein,
the assigning unit corrects the distance between a surface of the cell nucleus and the fluorescent bright point on the basis of a shape of the cell nucleus.

4. The image processing device of claim 3, wherein,
the assigning unit calculates an area of the cell nucleus and corrects the distance on the basis of the area.

5. The image processing device of claim 3, wherein,
the assigning unit calculates flatness of the cell nucleus and corrects the distance on the basis of the flatness.

6. An image processing device comprising:
an input unit to input a bright field image of a tissue slice in which a cell nucleus is stained and a fluorescent image of the tissue slice in which a specific biological substance is stained with a fluorescent staining reagent;
a first extracting unit to extract a cell nucleus from the bright field image;
a second extracting unit to extract a fluorescent bright point from the fluorescent image; and
an assigning unit to specify a cell nucleus to which the fluorescent bright point is assigned on the basis of a distance between the cell nucleus and the fluorescent bright point and to assign the fluorescent bright point to the cell nucleus, wherein,
the assigning unit sets a threshold for the distance between the cell nucleus and the fluorescent bright point and limits the cell nuclei to which the fluorescent bright point is assigned on the basis of an area of the cell nucleus or an N/C ratio of the cell.

7. An image processing device comprising:
an input unit to input a bright field image of a tissue slice in which a cell nucleus is stained and a fluorescent image of the tissue slice in which a specific biological substance is stained with a fluorescent staining reagent;
a first extracting unit to extract a cell nucleus from the bright field image;
a second extracting unit to extract a fluorescent bright point from the fluorescent image; and
an assigning unit to specify a cell nucleus to which the fluorescent bright point is assigned on the basis of a distance between the cell nucleus and the fluorescent bright: point and to assign the fluorescent bright point to the cell nucleus, wherein,
the assigning unit sets a threshold for the distance between the cell nucleus and the fluorescent bright point and limits the cell nuclei to which the fluorescent bright point is assigned on the basis of distances between vertexes of a predetermined frame which is assumed. to include the cell nucleus and the fluorescent bright point.

8. The image processing device of claim 6, comprising:
an excluding unit to exclude a fluorescent bright point after assignment processing from the assigned fluorescent bright points on the basis of an average distance between a surface of the cell nucleus and the fluorescent bright point after assignment processing, inclination or angle between straight lines connecting the fluorescent bright points after assignment processing, or the N/C ratio of the cell to which the fluorescent bright point is assigned.

9. The image processing device of claim 7, comprising:
an excluding unit to exclude a fluorescent bright point after assignment processing from the assigned fluorescent bright points on the basis of an average distance between a surface of the cell nucleus and the fluorescent bright point after assignment processing, inclination or angle between straight lines connecting the fluorescent bright points after assignment processing, or the N/C ratio of the cell to which the fluorescent bright point is assigned.

* * * * *